(12) United States Patent
Gillick et al.

(10) Patent No.: US 6,755,854 B2
(45) Date of Patent: *Jun. 29, 2004

(54) CONTROL DEVICE AND MECHANISM FOR DEPLOYING A SELF-EXPANDING MEDICAL DEVICE

(75) Inventors: Matthew J. Gillick, Temecula, CA (US); Kent C. B. Stalker, San Marcos, CA (US)

(73) Assignee: Advanced Cardiovascular Systems, Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/919,491

(22) Filed: Jul. 31, 2001

(65) Prior Publication Data

US 2003/0028236 A1 Feb. 6, 2003

(51) Int. Cl.⁷ .................................................. A61F 2/06
(52) U.S. Cl. ..................................................... 623/1.11
(58) Field of Search ............................... 623/1.11, 1.13, 623/1.15, 903; 606/108, 191, 194, 198, 200

(56) References Cited

U.S. PATENT DOCUMENTS

| | | | | |
|---|---|---|---|---|
| 5,160,341 A | * | 11/1992 | Brenneman et al. ......... | 606/198 |
| 5,618,300 A | * | 4/1997 | Marin et al. ................. | 604/106 |
| 5,707,376 A | * | 1/1998 | Kavteladze et al. ........ | 623/1.11 |
| 5,968,052 A | * | 10/1999 | Sullivan et al. ............. | 606/206 |
| 6,338,739 B1 | * | 1/2002 | Datta et al. ................. | 623/1.15 |
| 6,391,050 B1 | * | 5/2002 | Broome ...................... | 623/1.11 |
| 2002/0151955 A1 | * | 10/2002 | Tran et al. .................. | 623/1.12 |

* cited by examiner

*Primary Examiner*—Vy Q. Bui
(74) *Attorney, Agent, or Firm*—Fulwider Patton Lee & Utecht, LLP (57) ABSTRACT

A control device and mechanism for deploying a self-expanding medical device includes an actuating mechanism which allows the user to retract a restraining sheath from the self-expanding medical device by using a motion that is in angle to the line of motion of the restraining sheath, which helps prevent movement of the catheter portion of the control device within the patient. The control mechanism allows the physician to obtain a longer retracting stroke to the restraining sheath with a shorter actuating motion reducing the amount of manual actuation needed to be performed by the physician when retracting the sheath. The control mechanism can also reduce the amount of actuating force needed to retract the restraining sheath by utilizing springs or biasing members in connection with the actuating mechanism which combines with the actuating force supplied by the physician to cause the retraction of the restraining sheath.

29 Claims, 6 Drawing Sheets

CONTROL DEVICE AND MECHANISM FOR DEPLOYING A SELF-EXPANDING MEDICAL DEVICE

BACKGROUND OF THE INVENTION

The present invention relates to vascular catheters and devices, and more specifically to a control device for deploying self-expanding medical devices. Vascular catheters and devices are currently employed in a variety of medical procedures. These procedures often require manipulation (or actuation) of the vascular device by a mechanism located outside the patient's body. The present invention is specifically useful in deploying self-expanding medical devices, such as a self-expanding stent or graft, within a patient's vasculature.

Catheters have long been used in intraluminal procedures for various medical needs. They generally are made from elongated tubes which may be placed within various body lumens. A common use for catheters is the treatment of vascular diseases. Such procedures usually involve the percutaneous introduction of an interventional device into the lumen of the artery, usually through the catheter. One widely known and medically accepted procedure is balloon angioplasty in which an inflatable balloon is introduced within the stenosed region of the blood vessel to dilate the occluded vessel. The uninflated balloon catheter is initially inserted into the patient's arterial system and is advanced and manipulated into the area of stenosis in the artery. The balloon is inflated to compress the plaque and press the vessel wall radially outward to increase the diameter of the vessel, resulting in increased blood flow. The balloon is then deflated to a small profile so that the dilatation catheter can be withdrawn from the patient's vasculature. Enhanced blood flow should now resume in the dilated artery. As should be appreciated by those skilled in the art, while the above-described procedure is typical, it is not the only method used in angioplasty.

In the procedure of the kind referenced above, abrupt reclosure may occur or restenosis of the artery may develop over time, which may require another angioplasty procedure, a surgical bypass operation, or some other method of repairing or strengthening the injured area. To reduce the likelihood of the occurrence of abrupt reclosure and to strengthen the area, a physician can implant an intravascular prosthesis for maintaining vascular patency, commonly known as a stent, inside the artery across the lesion. The stent can be crimped onto the balloon portion of the catheter and transported in its delivery diameter through the patient's vasculature. At the deployment site, the stent is expanded to a larger diameter, often by inflating the balloon portion of the catheter.

A variety of stent designs have been developed and include self-expanding stents insertable and deliverable through the patient's vasculature in a compressed state for deployment in a body. Unlike balloon expandable stents which rely on an external radial force to expand the stent at the area of treatment, self-expanding stents are made from materials which are self-expanding in order to move between a compressed or collapsed position to an expanded, implanted position. Stent delivery catheters used for implanting self-expanding stents usually include an inner member upon which the compressed or collapsed stent is mounted and an outer restraining sheath placed over the stent to maintain it in its compressed state prior to deployment. When the stent is to be deployed in the body vessel, the outer restraining sheath is retracted in relation to the inner member to uncover the compressed stent, allowing the stent to immediately move into its expanded condition for implantation in the patient.

Vascular grafts also can be implanted within a body vessel utilizing a delivery catheter which is percutaneously introduced into the patient's vasculature system. These types of grafts may include a number of self-expanding rings, or small stents, placed along a flexible tubular member that forms a conduit once implanted in a body vessel. Vascular grafts are utilized to bypass diseased and weakened body vessels, such as when an artery experiences an aneurysm which weakens and abnormally expands the artery. In this manner, the vascular graft will act as a conduit for blood to flow freely there through, bypassing the diseased portion of the arterial wall caused by the aneurysm. As a result, the chances that the artery could possibly rupture due to pressure build-up in the artery is greatly reduced. Self-expanding vascular grafts also can be mounted onto a delivery catheter which includes a restraining sheath placed over the entire vascular graft, including the self-expanding rings, in order to maintain the graft in a collapsed position. Once the physician is able to manipulate the vascular graft into the desired location in the patient's vasculature, the simple retraction of the restraining sheath from the vascular graft will cause the self-expanding rings or stents to expand and contact the wall of the body lumen in which the graft is implanted.

These various treatments at the intraluminal site typically require the manipulation of the catheter system, a portion of which remains external to the patient's body. The physician must actuate the catheter system to retract the restraining sheath in order to properly deploy the stent or vascular graft in the body vessel. Actuator mechanisms which can be located at the proximal end of the catherter system may be as simple as a control handle attached to the restraining sheath that can be manipulated by the physician to retract the restraining sheath from the self-expanding medical device. During the placement of a stent or graft, it is important that the retraction of the restraining sheath be performed while the main catheter, on which the stent or graft is mounted, remains stationery in the body lumen. Some control mechanisms for retracting the restraining sheath requires that some force be applied by the physician in the longitudinal direction of the delivery catheter (i.e., in an axial direction). This force, in turn, can be transmitted to the main catheter assembly which can cause the stent or graft to move from the desired location within the body lumen. As the physician retracts the sheath, if the main catheter holding the stent or graft moves proximally with the sheath out of the target area, precision placement of the medical device will not be accomplished. Therefore, when a physician uses this type of device, the mere act of retracting the restraining sheath can sometimes result in inaccurate placement of the medical device within the body vessel.

Another problem exists when self-expanding stents or grafts which have an appreciable length (for example, 60 mm and longer) are to be deployed. These larger devices usually are more difficult to deploy accurately using existing catheter systems because a long retraction stroke is needed to retract the distal end of the restraining sheath from the medical device. In such cases, the physician may experience some difficulties in moving the proximal control device the required length to fully expose the self-expanding medical device. Moreover, the deployment of longer stents and grafts may require higher forces to retract the restraining sheath due to frictional forces which can be generated between the stent or graft and the restraining sheath as the sheath is being retracted. Therefore, the physician may have to apply more force to adequately retract the restraining sheath when a long stent or graft is being implanted. Thus, when a long stent or graft is being implanted, a physician may find it difficult to manipulate the proximalcontrol device while maintaining the remainder of the catheter system stationary to prevent the stent or graft from moving from the desired area of implantation.

Thus, what has been needed is a control mechanism which helps to provide a more precise deployment of a self-expanding medical device within the body vessel to reduce the chances that the physician may inadvertently move the medical device from the intended area of treatment. An improved control device is also needed when a long stent or graft to be deployed to reduce the actuating force which is needed to retract the sheath the required distance. Such a device also should reduce the length of the actuating motion which must be applied to the control device when retracting the restraining sheath. The present invention satisfies these and other needs.

SUMMARY OF THE INVENTION

The present invention provides a control device and mechanism for retracting a restraining sheath used in conjunction with self-expanding medical devices, such as self-expanding stents and vascular grafts, for implantation in a patient's vasculature.

The control device and mechanism of the present invention are particularly advantageous since the actuating mechanism allows the physician to retract the restraining sheath from the self-expanding medical device by using a motion that is at an angle to the line of motion of the restraining sheath, which should help to prevent movement of the catheter portion of the control device within the patient In one particular aspect of the present invention, the actuating motion can be substantially perpendicular to the line of motion of the proximal end of the restraining sheath. As a result, the physician's manipulation of the control device, when retracting the restraining sheath, should not place a displacing force on the inner portion of the catheter which could otherwise cause the stent or graft to move from the target area. A more accurate placement of a stent or graft can thus be accomplished by the physician since the possibility of stent or graft movement is reduced when the restraining sheath is being retracted. The control mechanism also allows the physician to deploy a longer stent or graft with a shorter actuating motion to reduce the amount of manual actuation performed by the physician when retracting the restraining sheath. As a result, the physician only needs to push a thumb knob or trigger a short distance to cause the restraining sheath to retract a larger distance to fully expose the medical device for implantation. The present invention also can use springs or biasing members to reduce the amount of force needed to push the knob or trigger. As a result, a physician will find that it is much easier to manipulate a control device made in the present invention especially when longer stents or vascular grafts are being deployed in the patient's vasculature.

In one aspect of the present invention, the control device utilizes a movable rack and pinion mechanism for retracting the proximal end of the restraining sheath while maintaining the inner catheter portion, on which the self-expanding medical device is mounted, stationary. The physician can grasp the control device and utilize his/her thumb to push a control knob attached to the moveable rack which causes rotation of a pinion and an attached pulley. Rotation of the pulley causes a timing belt to translate along the housing of the control device to move a slider member towards the pulley. The slider is attached to the proximal end of the restraining sheath so that when the slider is retracted proximally by the control mechanism, the distal end of the restraining sheath also will be retracted proximally the same distance to expose the stent or vascular graft. The moveable rack is designed to translate in a direction set at an angle, usually between 30° to 90°, to the line of motion defined by the slider/restraining sheath. As a result, when utilizing this type of mechanism, the physician does not have to move the control device in the same axial direction as the motion of the restraining sheath to retract the sheath for deployment purposes. Thus, the chances of the stent or vascular graft becoming displaced from the desired area of implantation in the body vessel is greatly reduced.

In another aspect of the present invention, the ratio of the pulley pitch diameter to the pinion pitch diameter can be increased to allow the physician to retract the restraining sheath a longer distance with only a minimal amount of actuating distance when manipulating the control knob. As a result, a long stent or graft can be more easily deployed with a minimal amount of actuating movement required by the physician. The moveable rack also can be spring loaded in order to reduce the amount of force needed to move the control knob when retracting the restraining sheath. In this manner, the physician does not need to use as much strength when using the actuating mechanism, which is especially useful when a long stent or vascular graft is being deployed. In this manner, the spring or biasing element utilized in conjunction with the moveable rack assists in pushing the movable rack along with the actuating motion provided by the physician.

It is to be understood that the present invention is not limited by the embodiments described herein. Other features and advantages of the present invention will become more apparent from the following detailed description of the invention, when taken in conjunction with the accompanying exemplary drawings.

DETAILED DESCRIPTION OF THE PREFERRED EMBODIMENTS

Turning now to the drawings, in which like reference numerals represent like or corresponding elements in the drawings, FIGS. 1–4 illustrate a control device 20 incorporating features of the present invention. This control device 20 is adapted for use with a medical device, such as a self-expanding stent or vascular graft. FIGS. 1–4 show a particular embodiment of a control device 20 incorporating features of the present invention which includes a housing 22 in which a control mechanism 24 (see FIGS. 2–4) is mounted. The control device 20 includes a catheter portion including a restraining sheath 26 which extends out from the housing 22 and extends to a distal end 28 where a self-expanding medical device, such as a stent 30 (see FIGS. 6 and 7) is maintained in a collapsed state ready for delivery into the patient's vasculature. The control device 20 includes a control knob 32 (FIG. 1) which can be manipulated by the physician to retract the restraining sheath 26 to deploy the stent 30 in the body vessel. This control knob 32 moves along a slot 34 in a top plate 36 which forms part of the housing 22. A bottom plate 38, shown better in FIGS. 2 and 3, forms the lower part of the housing 22 upon which the control mechanism 24 is mounted.

In use, the physician grasps the hand portion 40 of the control device and utilizes his/her thumb or index finger to move the control knob 32 in an upward motion to retract the restraining sheath 26 in order to deploy the stent 30. This control knob 32 is connected to a moveable rack 42 which remains in contact with a pinion gear 44 that is mounted onto a hub 46 formed on the bottom plate 38. The translation of the moveable rack 42 causes the pinion gear 44 to rotate which in turn rotates another gear or pulley 48 attached to the pinion gear 44. This pulley 48 is in turn connected to a timing belt 50 connected to a slider 52 that translates in a channel 54 formed on the bottom plate 38. This slider 52 is connected to the proximal end 56 of the restraining sheath 26 and causes the proximal end 56 to retract back in a linear motion within the housing 22 as the timing belt 50 moves the slider 52 proximally towards the pulley 48. In this manner, the distal end 28 of the restraining sheath 26 is retracted back to deploy the self-expanding stent 30.

As can be seen by the particular construction of this control mechanism 24, the travel of the slider 52 on the control device 20 is made in a line of motion which is accordingly parallel to the line of travel of the proximal end of the restraining sheath 26. The moveable rack 42, which is manipulated by the physician via the control knob 32, also translates in a linear motion that is substantially perpendicular to the line of motion of the slider 52 and, hence, the restraining sheath. In this manner, the physician can manipulate the proximal end 56 of the restraining sheath 26 with a hand motion which should not cause the stent 30 to move longitudinally within the body vessel once positioned in the patient's vasculature. Thus, a more precision placement of the medical device can be made by the physician since the risk of moving the self-expanding device with the retraction of the sheath is greatly reduced.

Figure 1:
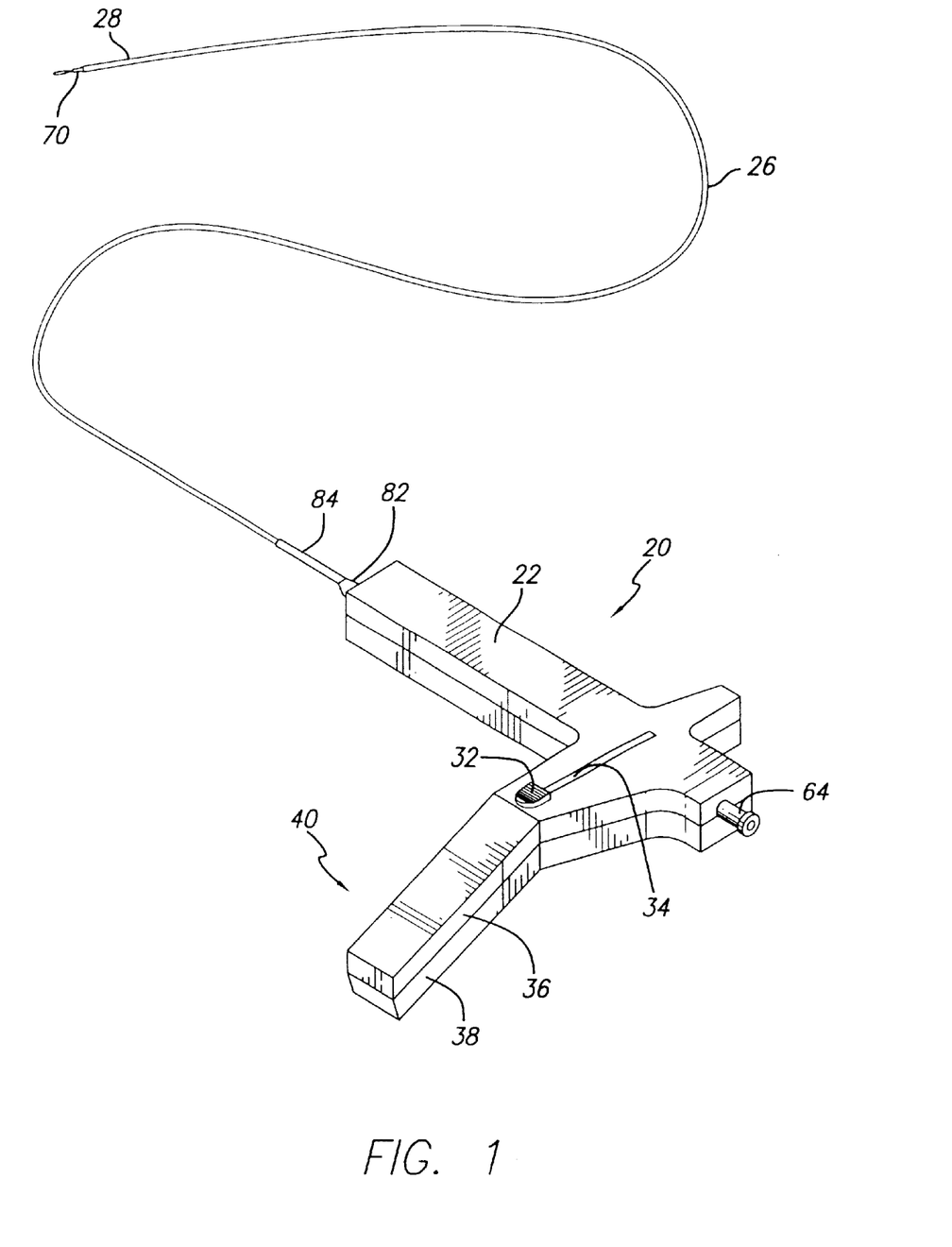
FIG. 1 is a perspective view of a control device and control mechanism embodying features of the present invention.
Figure 2:
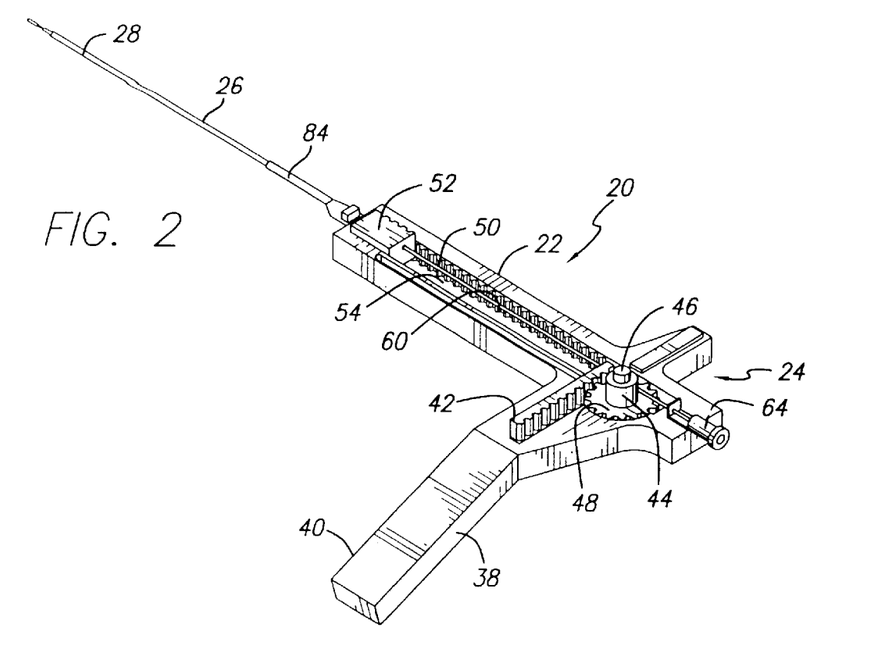
FIG. 2 is a perspective view of the control device and control mechanism of FIG. 1 with the top plate removed to better show the particular control mechanism embodying features of the present invention.
Figure 3:
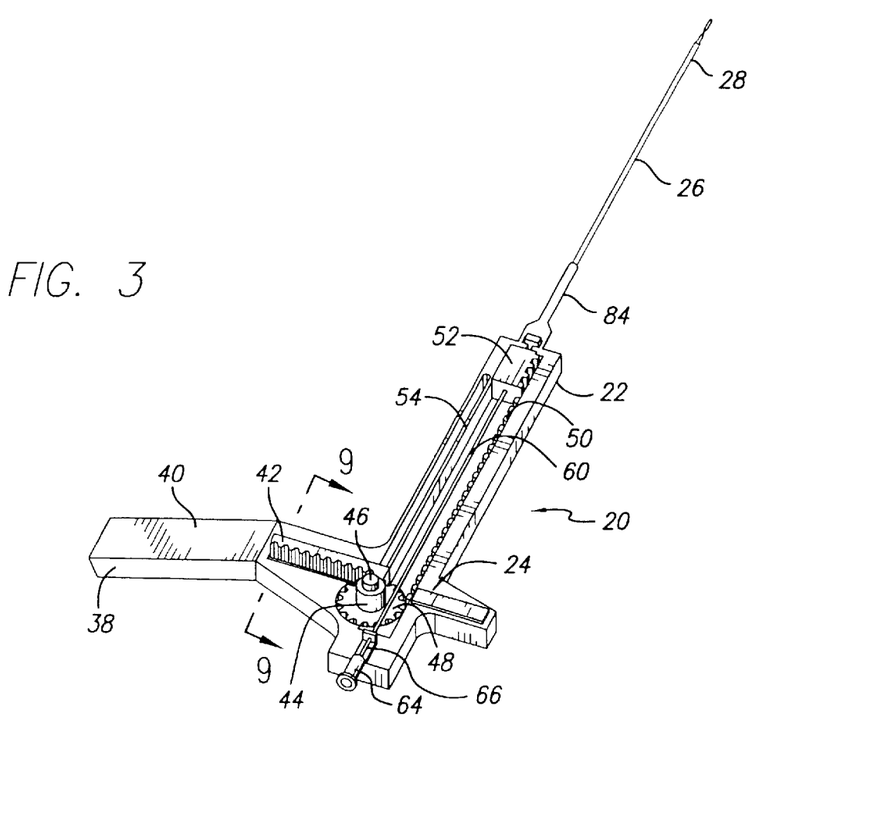
FIG. 3 is another perspective view showing the particular control mechanism of FIGS. 1 and 2.
Figures 4, 5, 6, 7:
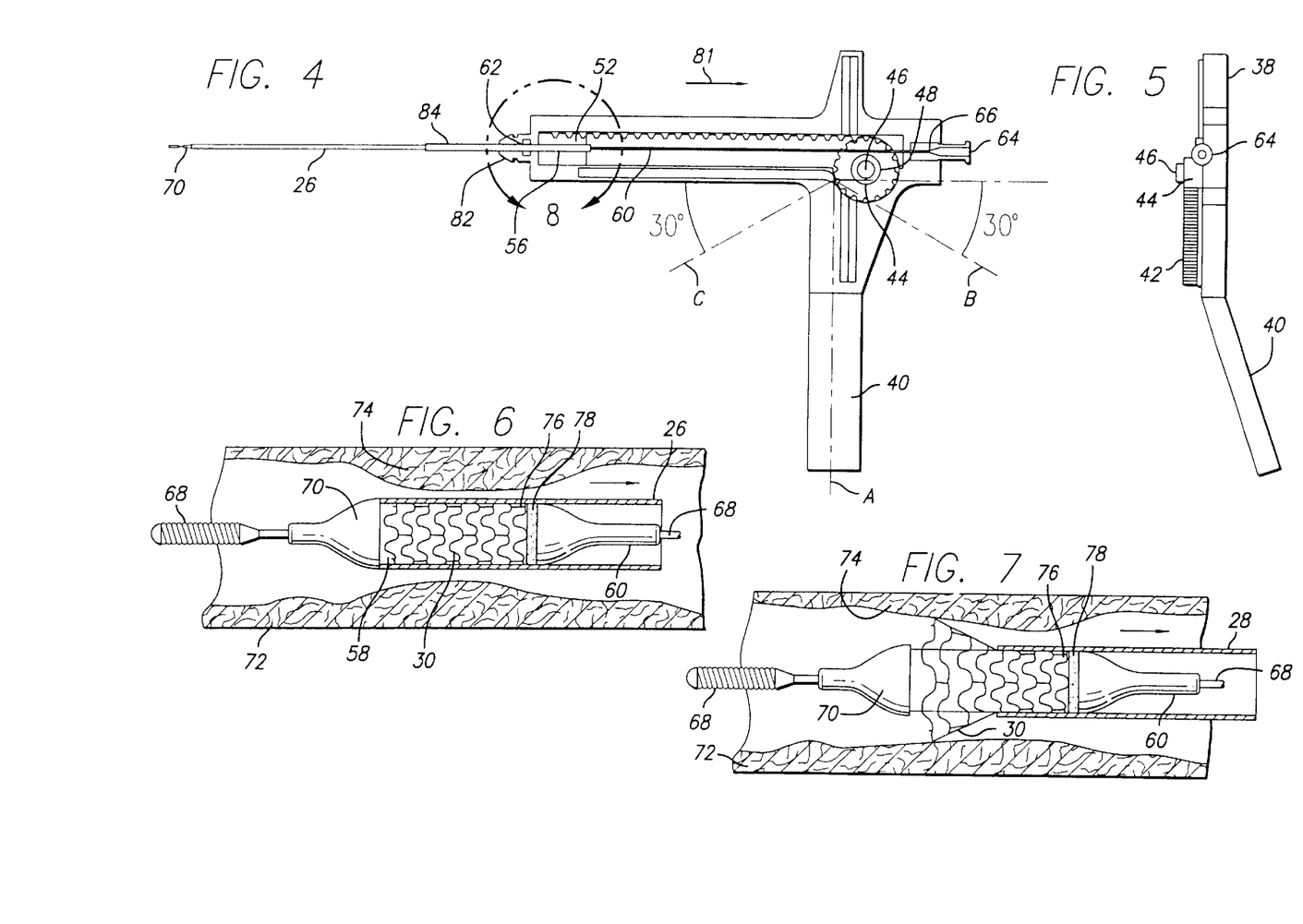
FIG. 4 is a plane view of the control device and control mechanism of FIGS. 1 and 2.
FIG. 5 is a side elevational view of the control device and control mechanism of FIGS. 1 and 2.
FIG. 6 is a side elevational view of the distal end of the catheter portion of the control device which shows a self-expanding stent being maneuvered into a diseased portion of a body vessel.
FIG. 7 is an elevational view similar to FIG. 6 which shows the distal end of the restraining sheath being retracted to deploy the self-expanding stent in the area of treatment in the body vessel.

Referring specifically to FIG. 4, the hand portion 40 and moveable rack (not shown in FIG. 4) are substantially perpendicular to the line of motion of the slider 52 within the channel 54 formed on the bottom plate 36 of the housing 22. A dotted line designated "A" in FIG. 4 shows the substantial 90° angle which the hand portion 40 and moveable rack 42 makes with the line of motion for the slider 52 and restraining sheath 26. Also, as is shown in FIG. 4, the hand portion 40 and moveable rack 42 could be placed at other angles besides 90° to the line of motion for the slider/sheath. For example, dotted lines "B" and "C" in FIG. 4 show the locations where the hand portion 40 and movable rack 42 could be positioned from the line of motion of the slider/sheath as well. This angle is shown to be about 30.° The position of the hand portion 40 and moveable rack 42 could be anywhere between these dotted lines "B" and "C" if desired. If an angle of less than about 30° is utilized, there still exists the possibility that the actuation of the control knob by the physician may cause some longitudinal movement to the catheter portion which will in turn move the placement of the stent or graft within the patient's vasculature. However, if the hand portion 40 and moveable rack 42 are located somewhere between dotted lines "B" and "C", there should be a minimal chance of catheter movement when the control knob is manipulated by the physician.

As can be seen in FIGS. 6 and 7, the stent 30 is mounted onto a mounting component 58 located at the distal end 28 of the restraining sheath 26. This mounting component 58 is in turn attached to an inner member 60 which extends coaxially with the restraining sheath 26 and is mounted within the control device 20. This inner member 60 and mounting component 58 also form a part of the catheter portion of the device 20. This inner member 60 extends through an opening 62 in the housing 22 to a leur fitting 64 which connects to the proximal end 66 of the inner member 60. This inner member 60 serves as a conduit for receiving a guide wire 68 (see FIGS. 6 and 7) utilized to deliver the medical device into the patient's artery, as will be explained in greater detail below. This inner member 60 can be made from a hypotube or other similar materials which provides axial strength to the catheter system. In use, this inner member 60 and the mounting component 58 must remain relatively stationary during the deployment of the stent otherwise the stent may be improperly implanted in the patient's vasculature. An obturator 70 creates an atraumatic tip for the catheter portion of the control device to prevent snowplowing of the distal end of the restraining sheath 26 as it moves through the patient's vasculature in an over-the-wire fashion along the guide wire 68. As can be seen in FIG. 6, this obturator is coned-shaped and is flush with the outer surface of the restraining sheath 26 to create a relatively smooth surface that helps to prevent snowplowing from occurring in the patient's vasculature.

In use, the self-expanding stent 30 would be delivered within a body vessel of the patient, such as an artery 72, as shown in FIGS. 6 and 7. The delivery of the stent 30 can be accomplished in the following manner. The stent 30 is first mounted onto the mounting component 58 of the inner catheter member 60 with the restraining sheath 26 being placed over the contracted stent. The catheter/stent assembly can then be introduced within the patient's vasculature in a conventional Seldinger technique through a guiding catheter (not shown). The guide wire 68 would be initially steered into the area of treatment where a stenosis 74 is located. The catheter/stent would then be advanced over the guide wire 68 until the stent 30 is directly under the stenosis 74. The restraining sheath 26 can then be retracted, allowing the stent 30 to expand to its larger diameter to press upward against the artherosclerosic plaque which has built up on the vessel wall, as illustrated in FIG. 6. While not shown in the drawing, the artery 72 is preferably expanded slightly by the expansion of the stent 30 to seat or otherwise fix the stent 30 to prevent movement. In some circumstances during the treatment of the stenoic portions of an artery, the artery may have to be expanded considerably in order to facilitate passage of blood or other fluid therethrough. Once the restraining sheath 26 is retracted to expose the stent, as shown in FIG. 7, the stent will expand and compress the stenosis somewhat to enlarge the lumen through which blood flows.

It should be appreciated that although the stent 30 is shown being utilized to treat an area in which artherosclerosic plaque has built up against the wall of an artery, it could also be used to hold up a detached lining, or other abnormality, of the patient. Moreover, the stent 30 can be utilized in any one of a number of different body vessels, including but not limited to carotid arteries, coronary arteries and renal arteries. The stent could be used for primary stenting purposes, i.e., to directly enlarge the opening in the artery, or it could be utilized in conjunction with predilitation in which the stenoic plaque is initially expanded in the area of treatment by a balloon dilitation catheter. Thereafter, the stent 30 could be placed in the predilitated area of treatment to help restenosis and to maintain this diseased portion of the artery in an open position. As indicated above, the present invention can also be utilized in conjunction with other self-expanding medical devices, for example, a self-expanding graft which could be delivered to a particular area in the patient's vasculature for providing a fluid conduit that bypasses a diseased portion of a vessel wall to prevent the vessel wall from rupturing.

As is shown in FIGS. 6 and 7, as the restraining sheath 26 is retracted past the self-expanding stent, the proximal end 76 of the stent 30 may come in contact with a radiopaque marker 78 located on the mounting component 58 to provide a source of visualization for the physician during placement of the stent in the patient's vasculature. This radiopaque marker 78 serves as an abutting shoulder to help prevent the stent 30 from moving back with the restraining sheath as it is being retracted due to the frictional forces which may be generated between the moving sheath and outer surface of the stent. In this manner, the possibility that the stent can be pulled back along with the restraining sheath is reduced.

Figure 8:
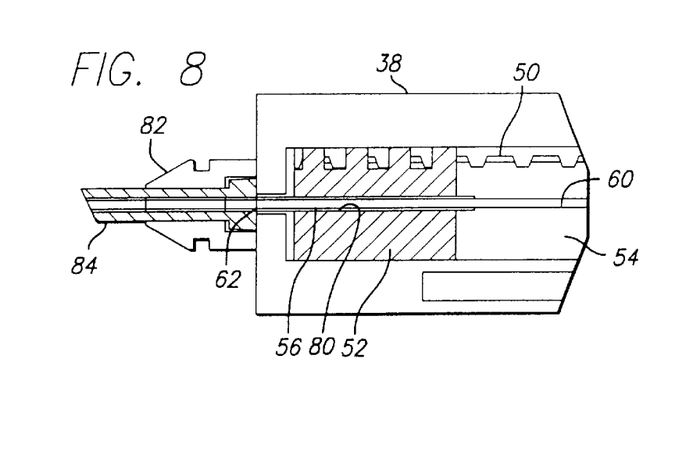
FIG. 8 is a side elevational view, partially in cross-section, of the slider member and timing belt which forms part of the control mechanism of FIGS. 1 and 2.

Referring specifically now to FIG. 8, the particular attachment utilized to connect the proximal end 56 of the restraining sheath 26 to the slider 52 is shown in greater detail. As can be seen in FIG. 8, the slider 52 translates within a channel 54 formed in the bottom plate 38 of the control handle 20 which follows the line of travel of the restraining sheath. The slider 52 includes an opening 80 through which the inner catheter member 60 and the proximal end 56 of the restraining sheath 28 extend through. However, the proximal end 56 of the restraining sheath 26 would be bonded within this opening 80 utilizing adhesives or other attachment techniques well-known in the art. As such, it would be securely affixed to the slider 52 and will move with the slider as it moves proximally towards the pulley 48 in the direction of the arrow 81 shown in FIG. 4. It should be appreciated that the restraining sheath 26 remains in a coaxial arrangement with the inner catheter member 60 as the restraining sheath 26 moves along the length of the inner catheter member 60 during deployment. The control mechanism 24 also helps to prevent the restraining sheath 26 from retracting prematurely since the slider 52 will remain at its position as shown in FIG. 4 until the pulley 48 is rotated via the action of the moveable rack 42. It should be appreciated by those skilled in the art that although a timing belt 50 is shown attached to the slider 52, the control mechanism could also utilize cables, pulleys and movable racks, and the like, to accomplish this same motion. Again, the deployment motion could be at an angle other than 90° to the line of motion of the retraining sheath. It also should be appreciated that the configuration of the hand portion could be altered to allow deployment of the stent by a whole hand motion, or by use of an individual finger, such as the thumb. Although a control knob 32 is shown and described as providing the mechanism for providing an upward motion to the moveable rack 42, the direction of this actuating motion could be in a opposite direction without departing from the spirit and scope of the present invention.

The control device 20 also may include a distal hub 82 at which a strain relief member 84 is located. This strain relief member 84 helps to prevent unwanted bending of the restraining sheath 26 at the distal end of the control device. Conventional strain relief components could be utilized in accordance with the present control device as illustrated in FIGS. 1–4.

Figure 9:
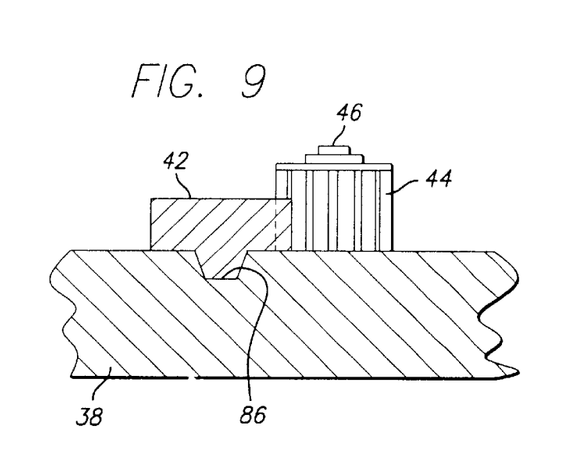
FIG. 9 is a side elevational view, partially in cross-section, taken along line 9—9 showing the moveable rack and pinion system used in accordance with the present invention.
Figure 10:
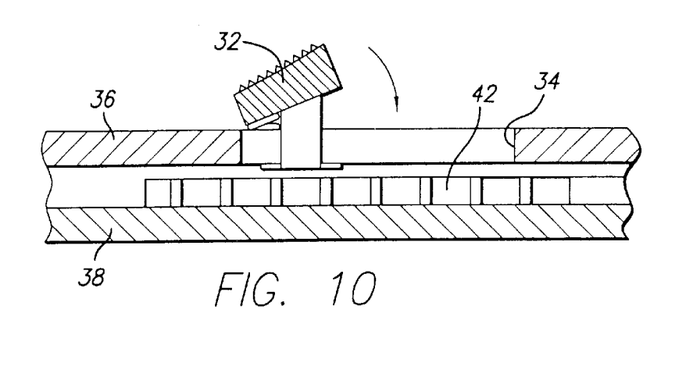
FIG. 10 is a side elevational view, partially in cross-section, showing the control knob and moveable rack which forms part of the control mechanism shown in FIGS. 1 and 2.
Figure 11:
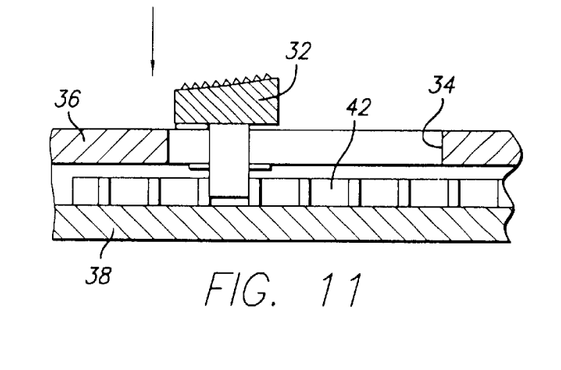
FIG. 11 is a side elevational view, partially in cross-section, showing the control knob of FIG. 10 as it is pushed down to contact the moveable rack when an actuating motion is to be applied to the control knob.

Referring now to FIGS. 4 and 9–11, the moveable rack 42 and control knob 32 are shown in greater detail. As can be seen in FIG. 9, the moveable rack 42 also translates within a channel 86 formed in the bottom plate 38 of the control handle 20. In this particular embodiment, the moveable rack 42 is designed to translate in a direction substantially perpendicular to the line of travel of the slider 52 and restraining sheath 26. The control knob 32 can be mounted onto the top plate 36 which forms part of the housing 22 in such a manner that the control knob will not engage the moveable rack 42 (as is shown in FIG. 10) until the physician is ready to retract the sheath 26. In this regard, a biasing element such as a spring (not shown) can be utilized to maintain the control knob 32 in an upright position (as shown in FIG. 10) until the physician desires to retract the restraining sheath 26. Thereafter, a slight downward push of the control knob 32 will engage the top portion of the moveable rack (as is shown in FIG. 11) to allow the physician to move the control knob 32 and movable rack 42 to retract the restraining sheath 26. Again, it should be appreciated that this is just one form of a control knob which can be utilized in accordance with the present invention and other variations of this actuating mechanism can be utilized without departing from the spirit and scope of the present invention.

Referring now specifically to FIG. 4, the diameters of the pinion gear 44 and pulley 48 can be seen. The upper pinion gear 44 has a smaller diameter than the pulley 48 utilized to translate the slider 52 within the channel 54. As a result, a particular ratio can be achieved which will result in a longer retracting stroke being applied to the restraining sheath 26 as the physician moves the control knob 32 to translate the moveable rack 42. In this manner, a greater retraction stroke can be achieved on the restraining sheath 26 by a smaller hand motion provided by the physician. This feature is certainly beneficial to the physician since less hand actuating would be required on his/her part in order to translate the restraining sheath a longer distance. This is particularly advantageous when a long stent is being deployed in the patient's vasculature which usually requires a long retracting stroke to fully retract the restraining sheath. This particular feature can be advantageous when a self-expanding vascular graft is the component to be deployed since vascular grafts are usually longer than self-expanding stents. It should be appreciate that any number of different gear ratios can be achieved in order to reduce the amount of hand motion needed by the physician to actuate the device while still achieving the desired retraction stroke to the sheath.

Although it is not shown in FIGS. 1–4, this moveable rack 42 can also be spring loaded to lower the force needed to be supplied by the physician when moving the control knob 32 to retract the restraining sheath 26. Such a spring could be located at the end of the moveable rack 42 to provide an external force to the moveable rack 42 as the control knob 32 is being manipulated by the physician. As a result, the physician need not apply as much force to move the control knob. Again, this feature can be useful when long stents or vascular grafts are being deployed since greater force is usually needed due to the increased amount of frictional contact created between the moving inner surface of the restraining sheath and the outer surface of the stent or graft.

Figure 12:
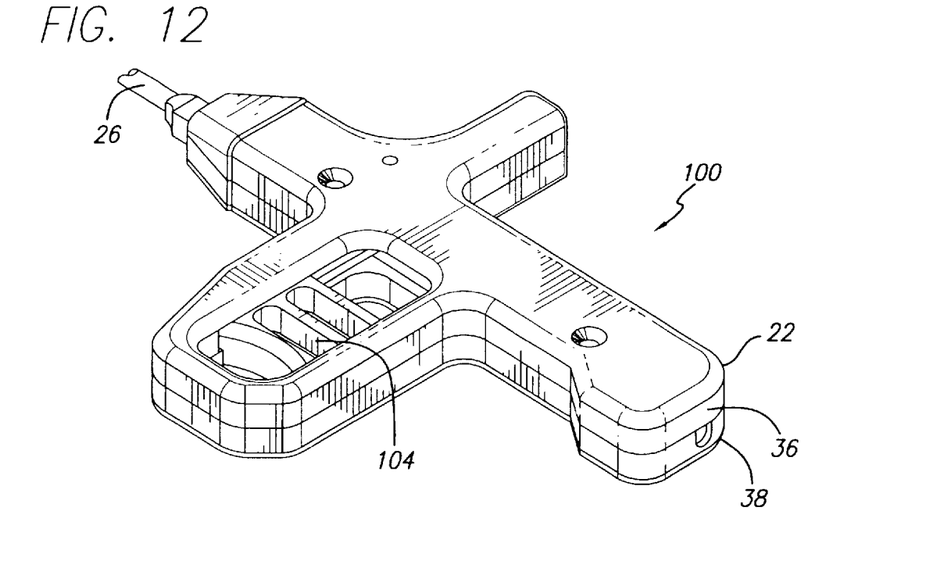
FIG. 12 is a perspective view of another embodiment of a control device and control mechanism made in accordance with the present invention.
Figure 13:
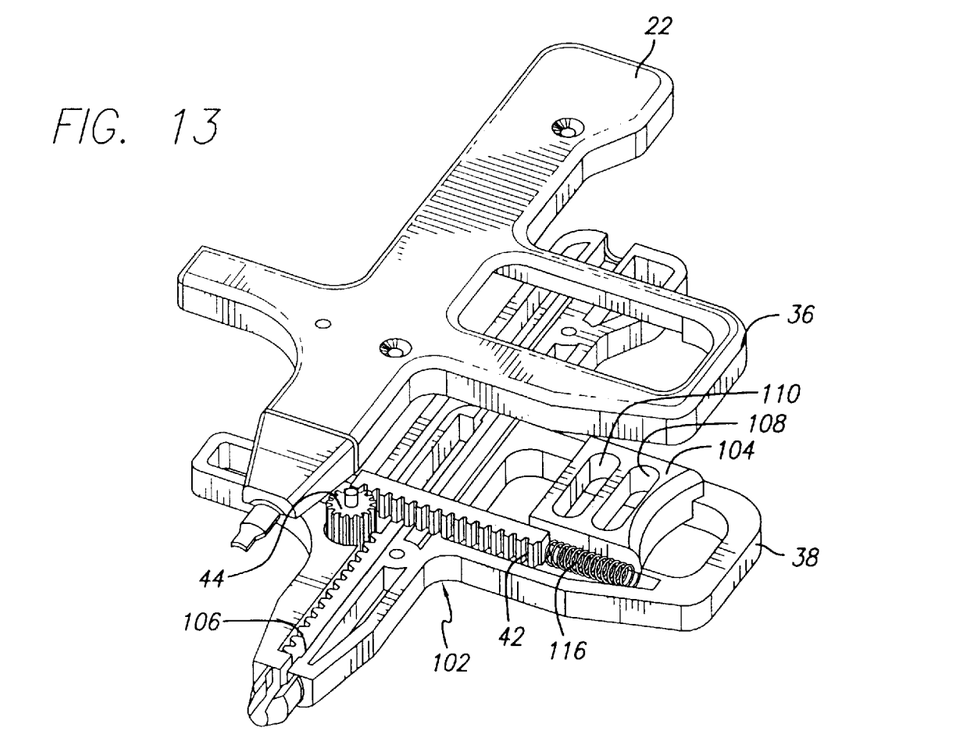
FIG. 13 is an exploded perspective view of the control device and control mechanism of FIG. 12.
Figure 14:
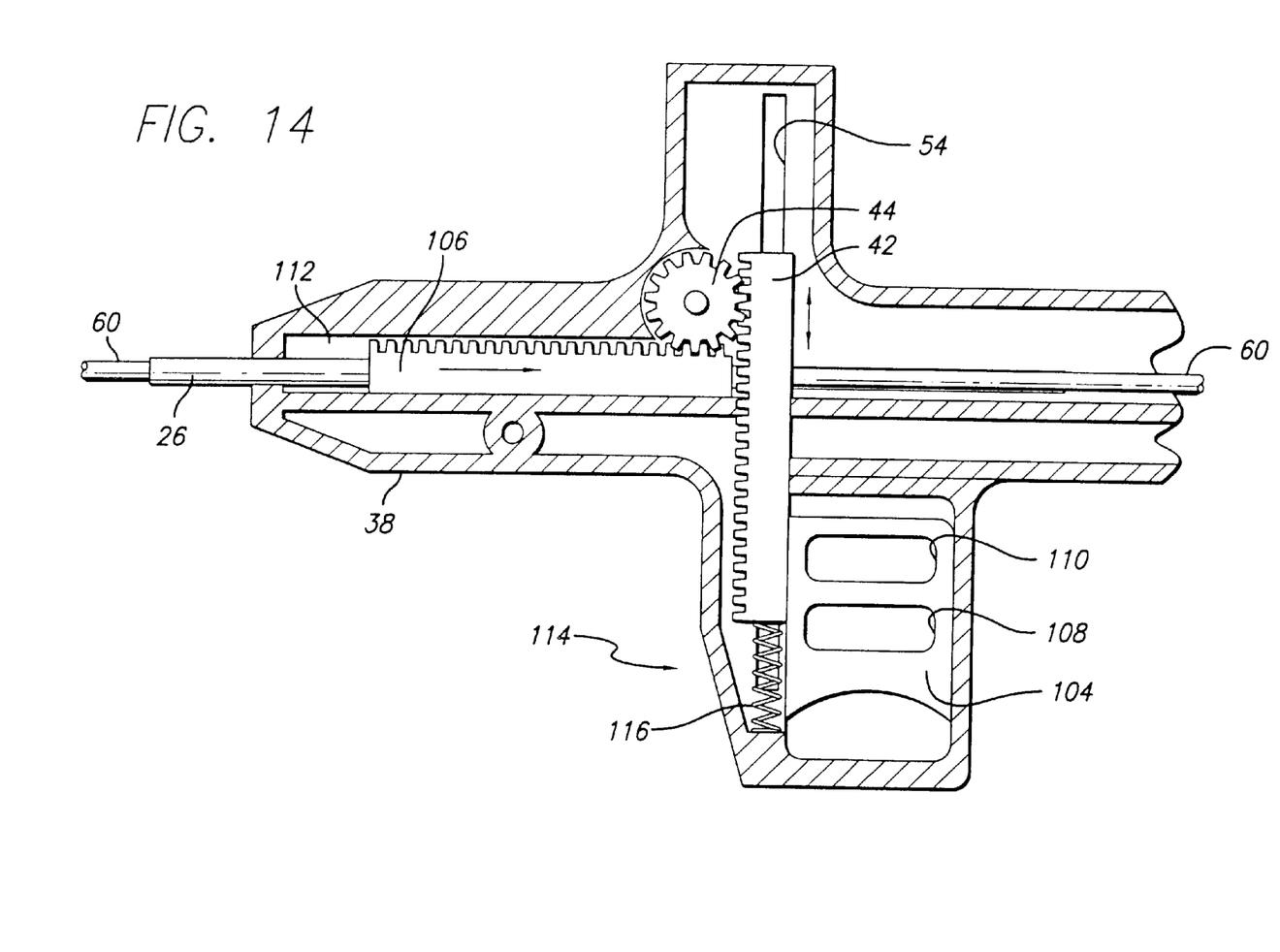
FIG. 14 is a plan view showing the control mechanism located in the control device of FIGS. 12 and 13.

Referring now to FIGS. 12–14, another embodiment of a control device 100 and control mechanism 102 made in accordance with the present invention is shown. In this particular embodiment, the control device 100 includes a housing 22 which include a bottom plate 38 and a top plate 36. This particular control device 100 and control mechanism 102 operates substantially as the previously described control device 20 in that the physician applies an actuating motion to the trigger 104 in a direction which is at an angle to the linear motion of the slider/restraining sheath in the housing. This angle can be between 30° and 150° with 90° being and optional angle when deploying the medical device. Referring specifically to FIGS. 13 and 14, the control device 100 includes a trigger 104 connected to a moveable rack 42 which contacts a pinion gear 44. A second moveable rack 106 which is attached to the proximal end of the restraining sheath 26 is in contact with this gear 44 or a second pulley or gear (not shown). As a result, the second moveable rack 106 moves in a linear motion that is at a substantially 90° angle to the motion of the first moveable rack 42. The trigger 104 of the control device 100 is designed with several openings 108 and 110 which are adapted to fit different sized hands of the physician using the control handle. In this manner, the movement of the trigger 104 by the physician should not cause the self-expanding medical device to move from the target in the patient's vasculature.

Referring specifically to FIG. 14, the second moveable rack 106 is shown as it is placed within a channel 112 formed in the bottom plate 38. The moveable rack 42 is also contained within a channel 54 and is, of course, attached to the trigger 104. In this particular embodiment, the gear ratio between the pinion gear 44 and the second gear also can be set so that only a small amount of actuating motion of the trigger will produce a long retraction stroke to the restraining sheath. The control device can be equipped with a spring loaded mechanism 114 which contacts the moveable rack 42 to provide a force which lowers the force which would be required by the physician when moving the trigger 104. For example, a spring 116 can be located in the channel 54 to contact one end of the moveable rack 42 to apply external force to the rack which again will help to reduce the amount of force needed when actuating the trigger.

The components of the present invention can be made from conventional plastics and polymeric materials known in the art. The lengths of the various components can vary depending upon the particular uses intended. For example, the length of the catheter portion of the control device can vary depending on the particular type of medical device to be implanted, the target location and the type of procedure to be administered.

Further modifications and improvements may additionally be made to the device and method disclosed herein without departing from the scope of the present invention. Accordingly, it is not intended that the invention be limited, except as by the appended claims.

What is claimed is:

1. A control device for deploying a self-expanding medical device within a body vessel, the control device comprising:

a restraining sheath having a proximal end and a distal end, the restraining sheath being adapted to extend over a self-expanding medical device to maintain the medical device in a collapsed position and to be retractable to expose the collapsed medical device for deployment; and a control mechanism including a slider assembly coupled to the proximal end of the restraining sheath for retracting the restraining sheath, the slider assembly being movable in a line of motion, the retraction of the restraining sheath being actuated by an actuating force applied by a user to a movable component of the control mechanism which moves in a linear path which is at a constant angle substantially different from zero degree to the line of motion of the slider assembly.

2. The control device of claim 1, wherein:

the angle at which the actuating force is to be applied to the movable component of the control mechanism is between about 30 and 90 degrees with the line of motion of the slider assembly.

3. The control device of claim 1, wherein:

the angle at which the actuating force is to be applied to the movable component of the control mechanism is substantially perpendicular to the line of motion of the slider assembly.

4. The control device of claim 1, wherein:

the actuating force placed on the movable component of the control mechanism causes translation of the movable component, the control mechanism causing the length of retraction of the restraining sheath to be larger than the length of translation of the movable component.

5. The control device of claim 4, wherein:

the control mechanism includes means for varying the length of retraction of the restraining sheath in response to the length of translation of the movable component.

6. The control device of claim 4, wherein:

the control mechanism includes means for reducing the amount of actuating force needed to translate the movable component to fully retract the restraining sheath from the medical device.

7. The control device of claim 6, wherein:

the means for reducing the amount of actuating force needed to translate the movable component are biasing means coupled to the movable component which places a force on the movable component in the direction of translation of the movable component.

8. The control device of claim 1, further including:
an elongate inner member upon which the restraining sheath is coaxially disposed, the inner member having a proximal end coupled with the control mechanism and a distal end having a mounting portion for mounting the self-expanding medical device.

9. The control device of claim 8, further including:
a housing for the control mechanism, the proximal end of the restraining sheath being movable in the housing in a line of motion with the proximal end of the inner member being affixed within the housing to maintain the inner member stationary as the restraining sheath is being retracted.

10. The control device of claim 9, wherein:
the control mechanism includes a movable rack and pinion assembly mounted within the housing, the movable component being a movable rack adapted to receive the actuating force for retracting the retraining sheath, the pinion being coupled with the slider assembly.

11. A control device for deploying a self-expanding medical device within a body vessel, the control device comprising:
a housing;
a catheter system coupled with the housing, the catheter system including a restraining sheath having a proximal end and a distal end and an inner member having a proximal end mounted within the housing and a distal end having a mounting portion for mounting a self-expanding medical device, the restraining sheath being disposed over the inner member with the distal end of the restraining sheath being extendable over the self-expanding medical device to maintain the medical device in a collapsed position, the restraining sheath being retractable to expose the collapsed medical device for deployment; and
a control mechanism mounted within the housing and including slider assembly coupled to the proximal end of the restraining sheath for retracting the restraining sheath, the slider assembly being movable in a line of motion, the retraction of the restraining sheath being actuated by an actuating force applied by a user to a movable component of the control mechanism which moves in a linear path which is at a constant angle substantially different from zero degree to the line of motion of the slider assembly.

12. The control device of claim 11 wherein:
the proximal end of the restraining sheath is movable within the housing in a line of motion with the proximal end of the inner member being affixed within the housing to maintain the inner member stationary as the restraining sheath is being retracted.

13. The control device of claim 12, wherein:
the control mechanism includes a movable rack and pinion assembly mounted within the housing, the movable component being a movable rack adapted to receive the actuating force for retracting the retraining sheath, the pinion being coupled with the slider assembly.

14. The control device of claim 13, wherein:
the movable rack is coupled to biasing element which places a force on the movable rack which reduces the actuating force needed to translate the movable rack in order to retract the restraining sheath.

15. The control device of claim 11, wherein:
the angle at which the actuating force is to be applied to the moveable component of the control mechanism is between 30 and 90 with the line of motion of the sliding assembly.

16. The control device of claim 11, wherein:
the angle at which the actuating force is to be applied to the movable component of the control mechanism is substantially perpendicular to the line of motion of the sliding assembly.

17. The control device of claim 11, wherein:
the actuating force placed on the movable component of the control mechanism causes translation of the movable component, the control mechanism causing the length of retraction of the restraining sheath to be larger than the length of translation of the movable component.

18. The control device of claim 17, wherein:
the control mechanism includes means for varying the length of retraction of the restraining sheath in response to the length of translation of the movable component.

19. The control device of claim 18, wherein:
the control mechanism includes means for reducing the amount of actuating force needed to translate the movable component to fully retract the restraining sheath from the medical device.

20. The control device of claim 19, wherein:
the means for reducing the amount of actuating force needed to translate the movable component are biasing means coupled to the movable component which places a force on the movable component in the direction of translation of the movable component.

21. A control device for deploying a self-expanding medical device within a body vessel, the control device comprising:
an inner member having a proximal portion and a distal end and being adapted to receive a self-expanding medical device;
a restraining sheath adapted to extend over the self-expanding medical device to maintain the self-expanding medical device in a collapsed position, the restraining sheath being retractable to expose the self-expanding medical device for deployment; and
a control mechanism mounted within a housing, the control mechanism coupled with the restraining sheath for moving the restraining sheath to expose the self-expanding medical device, wherein the proximal portion of the inner member extends within the housing and defines a line of motion, the movement of the restraining sheath being accomplished by an actuating force applied by the user to a control member which moves in a linear path being at a constant angle substantially different from zero degree with the line of motion defined by the proximal portion of the inner member.

22. The control device of claim 21, wherein:
the direction of the actuating force applied by the user to the movable component of the control mechanism is between about 30 and 90 degrees with the line of motion defined by the proximal portion of the inner member.

23. The control device of claim 21, wherein:
the direction of the actuating force applied by the user to the movable component of the control mechanism is substantially perpendicular to the line of motion defined by the inner member.

24. The new control device of claim 21, wherein:

the inner member includes a lumen for receiving a guide wire.

25. A control device for deploying a self-expanding medical device within a body vessel, the control device comprising:

a housing;

a restraining sheath adapted to extend over the self-expanding medical device to maintain a self-expanding medical device in a collapsed position, the restraining sheath being retractable to expose the self-expanding medical device for deployment; and a control mechanism associated with the housing and coupled to the restraining sheath for moving the restraining sheath to expose the self-expanding medical device, the control mechanism including a control knob within the housing and a sliding component which moves substantially linearly within the housing, the sliding component being coupled to the restraining sheath and being movable by an actuating motion applied by the user to the control knob, which control knob moves in a linear fashion to form a constant angle substantially different from zero degree with the linear movement of the sliding component.

26. The control device of claim 25, wherein:

the movement of the control knob is substantially perpendicular to the linear movement of the sliding component.

27. A control device for deploying a self-expanding medical device within a body vessel, the control device comprising:

a restraining sheath having a proximal end and a distal end, the restraining sheath being adapted to extend over a self-expanding medical device to maintain the medical device in a collapsed position and to be retractable to expose the collapsed medical device for deployment;

an elongate inner member upon which the restraining sheath is disposed, the inner member having a mounting portion for mounting the self-expanding medical device; and a housing associated with a control mechanism, the control mechanism including a slider assembly movable within the housing and coupled to the proximal end of the restraining sheath for retracting the restraining sheath in a line of motion, the control mechanism including a movable rack and pinion assembly mounted within the housing, the movable rack being adapted to receive an actuating force for retracting the retraining sheath, the pinion assembly being coupled with the slider assembly, a gear connected to the pinion and means connecting the slider assembly to the gear for translating the slider assembly when the gear is rotated by the rotation of the pinion, the retraction of the restraining sheath being actuated by an actuating force applied by a user to the movable rack which moves in a linear direction which is at a constant angle substantially different from zero degree to the line of the restraining sheath, the proximal end of the inner member being affixed within the housing to maintain the inner member stationary as the restraining sheath is being retracted.

28. A control device for deploying a self-expanding medical device within a body vessel, the control device comprising:

a housing;

a catheter system coupled with the housing, the catheter system including a restraining sheath having a proximal end and a distal end and an inner member having a proximal end mounted within the housing and a distal end having a mounting portion for mounting a self-expanding medical device, the restraining sheath being disposed over the inner member with the distal end of the restraining sheath being extendable over the self-expanding medical device to maintain the medical device in a collapsed position, the restraining sheath being retractable to expose the collapsed medical device for deployment, the proximal end of the restraining sheath being movable within the housing and the proximal end of the inner member being affixed within the housing to maintain the inner member stationary as the restraining sheath is being retracted; and a control mechanism mounted within the housing, the control mechanism including a slider assembly coupled to the proximal end of the restraining sheath for retracting the restraining sheath in a line of motion, the retraction of the restraining sheath being actuated by an actuating force applied by a user to a movable rack which moves in a linear direction which is at a constant angle substantially different from zero degree to the line of motion of the restraining sheath, the control mechanism including a pinion assembly coupled with the slider assembly, a gear connected to the pinion assembly and means connecting the slider assembly to the gear for translating the slider assembly when the gear is rotated by the rotation of the pinion.

29. The control device of claim 28, wherein:

the gear has a larger diameter than the pinion to cause the length of retraction of the restraining sheath to be larger than the length of translation of the movable rack.

* * * * *

UNITED STATES PATENT AND TRADEMARK OFFICE
CERTIFICATE OF CORRECTION

PATENT NO. : 6,755,854 B2
DATED : June 29, 2004
INVENTOR(S) : Matthew J. Gillick and Kent C.B. Stalker It is certified that error appears in the above-identified patent and that said Letters Patent is hereby corrected as shown below:

<u>Title page,</u>
Item [75], Inventor, delete "Temecula" and insert -- Murrieta --.

<u>Column 2,</u>
Line 34, delete "catherter" and insert -- catheter --.

<u>Column 3,</u>
Line 5, delete "proximalcontrol" and insert -- proximal control --.
Line 36, after "patient" insert -- . -- (a period).

<u>Column 9,</u>
Line 12, delete "appreciate" and insert -- appreciated --.
Line 40, delete "and" and insert -- an --.

<u>Column 11,</u>
Line 60, delete "retraining" and insert -- restraining --.

<u>Column 13,</u>
Line 51, delete "retraining" and insert -- restraining --.

Signed and Sealed this

Second Day of August, 2005

JON W. DUDAS
*Director of the United States Patent and Trademark Office*